United States Patent
Hu et al.

(10) Patent No.: US 12,292,158 B2
(45) Date of Patent: May 6, 2025

(54) VERTICAL PROTECTIVE DEVICE FOR MEDICAL DISPLAY HANGER

(71) Applicant: Maquet (Suzhou) Co. Ltd., Suzhou (CN)

(72) Inventors: Qing Hu, Suzhou (CN); Jin Xuan, Suzhou (CN); Qunhua Li, Suzhou (CN)

(73) Assignee: Maquet (Suzhou) Co. Ltd., Suzhou (CN)

( * ) Notice: Subject to any disclaimer, the term of this patent is extended or adjusted under 35 U.S.C. 154(b) by 406 days.

(21) Appl. No.: 17/787,432

(22) PCT Filed: Jun. 18, 2020

(86) PCT No.: PCT/CN2020/096749
§ 371 (c)(1),
(2) Date: Jun. 20, 2022

(87) PCT Pub. No.: WO2021/120558
PCT Pub. Date: Jun. 24, 2021

(65) Prior Publication Data
US 2023/0012520 A1    Jan. 19, 2023

(30) Foreign Application Priority Data
Dec. 20, 2019    (CN) .......................... 201911324488.2

(51) Int. Cl.
*F16M 11/24*    (2006.01)
*A61G 12/00*    (2006.01)
(Continued)

(52) U.S. Cl.
CPC ........... *F16M 11/24* (2013.01); *A61G 12/002* (2013.01); *F16P 7/00* (2013.01); *A61B 50/28* (2016.02); *A61G 2203/80* (2013.01)

(58) Field of Classification Search
CPC ..... A61G 12/002; A61G 2203/80; F16P 7/00; F16P 7/02; A61B 50/28; F16M 11/24
(Continued)

(56) References Cited

U.S. PATENT DOCUMENTS

| 4,733,408 | A | | 3/1988 | Beikuefner et al. | |
|---|---|---|---|---|---|
| 4,987,583 | A | * | 1/1991 | Travanty | A61B 6/102 378/197 |
| 5,056,365 | A | * | 10/1991 | Gray | A61B 6/102 378/117 |

(Continued)

FOREIGN PATENT DOCUMENTS

| CN | 102058415 A | 5/2011 |
|---|---|---|
| CN | 202136349 U | 2/2012 |

(Continued)

OTHER PUBLICATIONS

European Patent Office, Extended European Search Report, Application No. 20901783.9, Jan. 2, 2024, 5 pages.
(Continued)

*Primary Examiner* — Christopher Garft
(74) *Attorney, Agent, or Firm* — Quarles & Brady LLP

(57) ABSTRACT

A vertical protective device for a medical display hanger comprises a contact piece, a microswitch, a rotating shaft and a vertical protective plate, wherein the contact piece is connected to one end of the rotating shaft, the vertical protective plate is connected to the other end of the rotating shaft, and the microswitch is arranged on a microswitch support; and when a collision of the vertical protective plate happens, the rotating shaft drives the contact piece to rotate, and the contact piece triggers the microswitch, so as to control the medical display hanger to stop moving or immediately rise. When an accidental collision of the medical display hanger happens in a substantially vertical direction, the medical display hanger can effectively come to an emergency stop.

8 Claims, 3 Drawing Sheets

(51) Int. Cl.
*F16P 7/00* (2006.01)
*A61B 50/28* (2016.01)

(58) Field of Classification Search
USPC .......................................................... 248/550
See application file for complete search history.

(56) References Cited

U.S. PATENT DOCUMENTS

| | | | | |
|---|---|---|---|---|
| 5,097,495 | A | * | 3/1992 | Gray ...................... A61B 6/102 |
| | | | | 378/91 |
| 5,909,938 | A | * | 6/1999 | Brenner .................... F16P 7/00 |
| | | | | 33/503 |
| 8,661,584 | B1 | | 3/2014 | Yang et al. |
| 2004/0143930 | A1 | * | 7/2004 | Haegermarck ...... G05D 1/0227 |
| | | | | 15/358 |
| 2016/0073839 | A1 | * | 3/2016 | Janzen ................ A47L 11/4061 |
| | | | | 15/3 |
| 2022/0202379 | A1 | * | 6/2022 | Nie ........................ A61B 6/102 |

FOREIGN PATENT DOCUMENTS

| | | |
|---|---|---|
| CN | 103654836 A | 3/2014 |
| CN | 105287010 A | 2/2016 |
| CN | 206297288 U | 7/2017 |
| CN | 109276317 A | 1/2019 |
| CN | 110848553 A | 2/2020 |
| CN | 211649777 U | 10/2020 |
| DE | 3343924 A1 | 6/1985 |
| EP | 2705796 A1 | 3/2014 |

OTHER PUBLICATIONS

PCT International Search Report and Written Opinion and translation thereof, PCT/CN2020/096749, Sep. 24, 2020, 16 pages.
The State Intellectual Property Office of People's Republic of China, First Office Action and Search Report, Application No. 201911324488.2, Dec. 23, 2024, 12 pages.

* cited by examiner

VERTICAL PROTECTIVE DEVICE FOR MEDICAL DISPLAY HANGER

CROSS-REFERENCE TO RELATED APPLICATIONS

This application represents the U.S. national stage entry of International Application No. PCT/CN2020/096749 filed Jun. 18, 2020, which claims priority to Chinese Application No. 201911324488.2 filed Dec. 20, 2019, the disclosure of which is incorporated herein by reference in its entirety and for all purposes.

TECHNICAL FIELD

The present invention relates to the technical field of medical instruments, and in particular to a vertical protective device for a medical display hanger.

BACKGROUND ART

Currently, in hybrid operating rooms, there are many kinds of expensive medical equipment and instruments to support complex operations. Medical display hangers are very close to operating tables and patients, and the medical display hangers are generally driven by electric arms. When medical staff use control buttons to drive (mainly lift) the medical display hangers, they may accidentally collide with the patients or surrounding medical equipment. Therefore, it is necessary to enable the medical display hanger to come to an emergency stop or avoid when the medical display hanger accidentally collides with surrounding people and/or objects in a substantially vertical (i.e., upright) direction.

SUMMARY OF THE INVENTION

An object of the present invention is to provide a vertical protective device for a medical display hanger, which can solve the problems existing in the prior art, so that when an accidental collision of the medical display hanger happens in a substantially vertical direction, the medical display hanger can effectively come to an emergency stop or avoid.

The above object of the present invention is achieved by a vertical protective device for a medical display hanger, the vertical protective device for the medical display hanger comprising a contact piece, a microswitch, a rotating shaft and a vertical protective plate, wherein the contact piece is connected to one end of the rotating shaft, the vertical protective plate is connected to the other end of the rotating shaft, and the microswitch is arranged on a microswitch support; and when a collision of the vertical protective plate happens, the rotating shaft drives the contact piece to rotate, and the contact piece triggers the microswitch, so as to control the medical display hanger to stop moving or immediately rise.

According to the above technical solution, the vertical protective device for a medical display hanger of the present invention can achieve the following beneficial technical effect: when an accidental collision of the medical display hanger happens in a substantially vertical direction, the medical display hanger can effectively come to an emergency stop or avoid.

Specifically, the present invention adopts a vertical protective device for a medical display hanger, when an accidental collision of the medical display hanger happens in a substantially vertical direction, the vertical protective plate rotates upwardly, such that the rotating shaft drives the contact piece to rotate, the contact piece triggers the microswitch, and the microswitch sends a signal to a controller, so as to control the medical display hanger to stop the descending movement or immediately rise, that is, the emergency stop or avoidance of the medical display hanger can be realized.

Preferably, when the medical display hanger is lowered and causes the collision of the vertical protective plate, the medical display hanger is controlled to stop moving.

According to the above technical solution, the vertical protective device for a medical display hanger of the present invention can achieve the following beneficial technical effect: when an accidental collision of the medical display hanger happens in a substantially vertical direction, the medical display hanger can effectively emergency stop.

Preferably, when an operating table rises and causes the collision of the vertical protective plate, the medical display hanger is controlled to rise immediately.

According to the above technical solution, the vertical protective device for a medical display hanger of the present invention can achieve the following beneficial technical effect: when an accidental collision of the medical display hanger happens in a substantially vertical direction, the medical display hanger can effectively avoid.

Preferably, the vertical protective device for the medical display hanger further comprises a rotating shaft support, and the rotating shaft is provided with one end passing through the rotating shaft support.

According to the above technical solution, the vertical protective device for a medical display hanger of the present invention can achieve the following beneficial technical effect: the rotation of the rotating shaft can be made stable, so that the medical display hanger can more effectively come to an emergency stop or avoid.

Preferably, the vertical protective device for the medical display hanger further comprises an internal limiting post and a limiting block, the internal limiting post is arranged on an inside face of the rotating shaft support, and the limiting block is arranged on the rotating shaft and opposite the internal limiting post; and when no collision of the vertical protective plate happens, the limiting block abuts against the internal limiting post due to the gravity of the vertical protective plate.

According to the above technical solution, the vertical protective device for a medical display hanger of the present invention can achieve the following beneficial technical effect: when no collision of the vertical protective plate happens, the vertical protective plate can be kept in a substantially horizontal state.

Preferably, the vertical protective device for the medical display hanger further comprises a handle support and an external limiting post, the handle support is connected to the rotating shaft support, and the external limiting post is arranged on the handle support; and when the collision of the vertical protective plate happens and the vertical protective plate rotates upwardly to a maximum upward rotation angle, the vertical protective plate interferes with the external limiting post to realize limiting.

According to the above technical solution, the vertical protective device for a medical display hanger of the present invention can achieve the following beneficial technical effect: the upward rotation angle of the vertical protective plate can be restricted within a certain range, so that the microswitch can be effectively triggered, and the microswitch can also be prevented from being damaged due to excessive contact.

Preferably, the maximum upward rotation angle of the vertical protective plate is 2-5 degrees.

According to the above technical solution, the vertical protective device for a medical display hanger of the present invention can achieve the following beneficial technical effect: by setting an appropriate maximum upward rotation angle of the vertical protective plate, the microswitch can be effectively triggered, and the microswitch can also be prevented from being damaged due to excessive contact.

Preferably, the maximum upward rotation angle of the vertical protective plate is 3.5 degrees.

According to the above technical solution, the vertical protective device for a medical display hanger of the present invention can achieve the following beneficial technical effect: by setting an optimal maximum upward rotation angle of the vertical protective plate, the microswitch can be effectively triggered, and the microswitch can also be prevented from being damaged due to excessive contact.

Preferably, the vertical protective device for the medical display hanger further comprises a bottom plate, the bottom plate is connected to the rotating shaft support, and the microswitch support is arranged on the bottom plate.

According to the above technical solution, the vertical protective device for a medical display hanger of the present invention can achieve the following beneficial technical effect: the microswitch can be installed in a rational position, so that the microswitch can be effectively triggered.

Preferably, when the operating table rises and causes the collision of the vertical protective plate, the medical display hanger is controlled to rise immediately at a rising speed of 25-30 mm/s.

According to the above technical solution, the vertical protective device for a medical display hanger of the present invention can achieve the following beneficial technical effect: when an accidental collision of the medical display hanger happens in a substantially vertical direction, the medical display hanger can more effectively avoid.

LIST OF REFERENCE SIGNS

Figure 1:
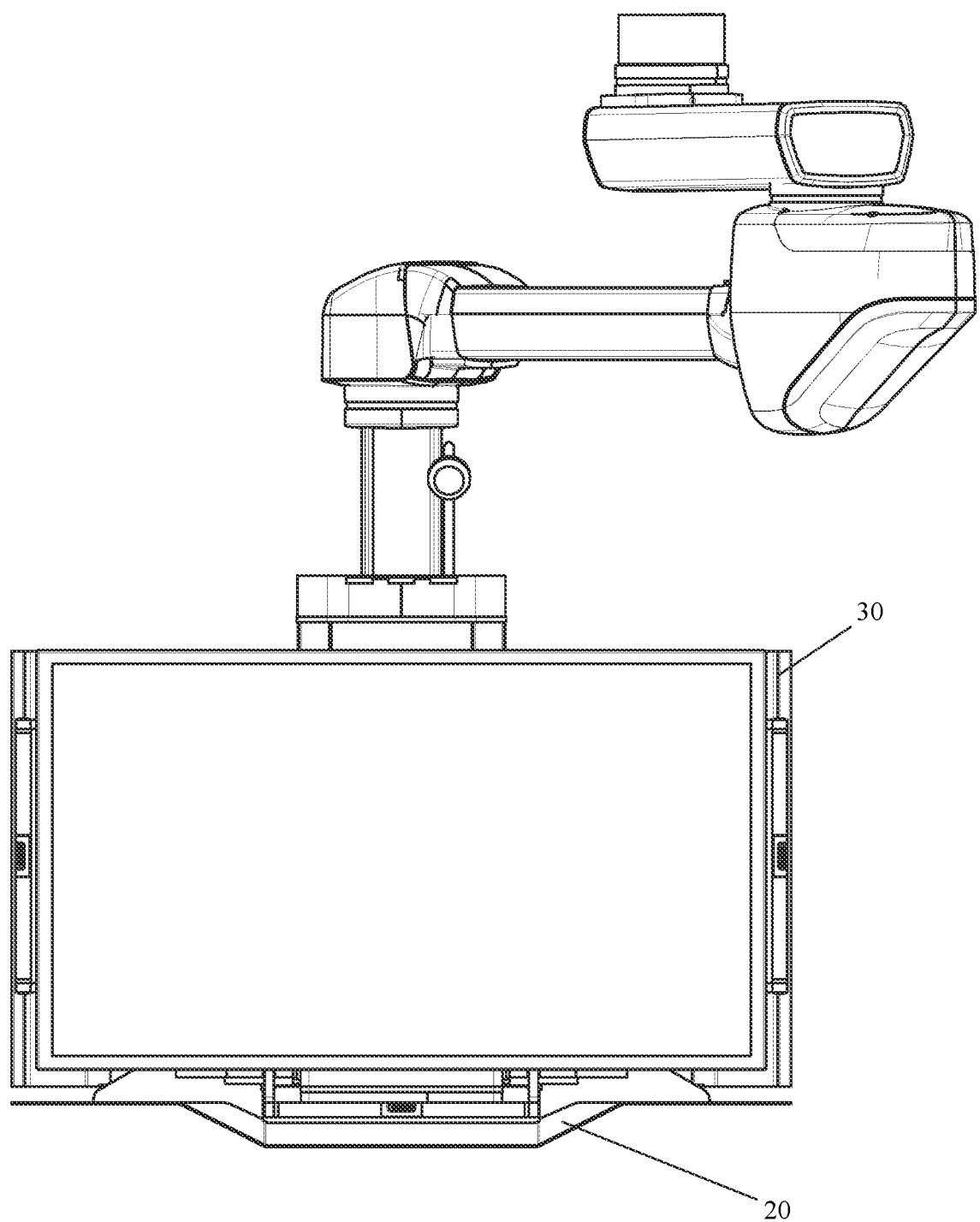
FIG. 1 is a schematic installation diagram of a vertical protective device for a medical display hanger according to an embodiment of the present invention.

1. Contact piece
2. Microswitch
3. Rotating shaft
4. Vertical protective plate
5. Limiting block
6. External limiting post
7. Internal limiting post
8. Rotating shaft support
9. Bottom plate
10. Microswitch support
11. Handle support
20. Vertical protective device for medical display hanger
30. Medical display hanger

DETAILED DESCRIPTION OF EMBODIMENTS

The specific embodiments of the present invention will be described below. It should be pointed out that in the detailed description of these embodiments, it is not possible for this description to describe in detail all the features of the actual embodiments for the sake of brevity and simplicity of description. It should be understood that in the actual implementation of any one embodiment, as in the course of any engineering project or design project, in order to achieve the developer's specific objectives and meet system-related or business-related constraints, a variety of specific decisions are often made, and thus any change may occur from one embodiment to another. Moreover, it is also understandable that although the efforts made during such development may be complex and lengthy, for those of ordinary skill in the art related to the disclosure of the present invention, some changes in design, manufacturing or production based on the technical content disclosed in the present disclosure are only conventional technical means, and it should not be understood that the content of the present disclosure is insufficient.

Unless otherwise defined, the technical terms or scientific terms as used in the claims and the description should be construed in a generic meaning as understood by those of ordinary skill in the art to which the present invention pertains. The terms "first", "second" or the like as used in the description and claims of the patent application of the present invention do not denote any order, quantity, or importance, but are merely used to distinguish different components. The terms "a", "an" or the like do not denote a quantity limitation but mean that there is at least one. The terms "include", "comprise" or the like mean that the elements or objects that precede "include" or "comprise" encompass the elements or objects and their equivalents that appear after "include" or "comprise" and do not exclude other elements or objects. The terms "connect", "connected" or the like are not limited to physical or mechanical connections, nor are they limited to direct or indirect connections.

It should be noted that the terms "upper", "lower", "front", "rear", "left", "right", etc. used herein are exemplary directions defined only for facilitating the description of the present invention. As shown in FIG. 1, the direction toward the reader is "front", and the direction away from the reader is "rear", the direction of the bottom side in the paper is "lower", the direction of the top side in the paper is "upper", the direction of the left side in the paper is "left", and the direction of the right side in the paper is "right". Of course, on the basis of the present invention, those skilled in the art would be able to understand that the directions such as "upper", "lower", "front", "rear", "left", and "right" can be defined in other ways, which also fall within the scope of protection of the present invention.

Figure 2:
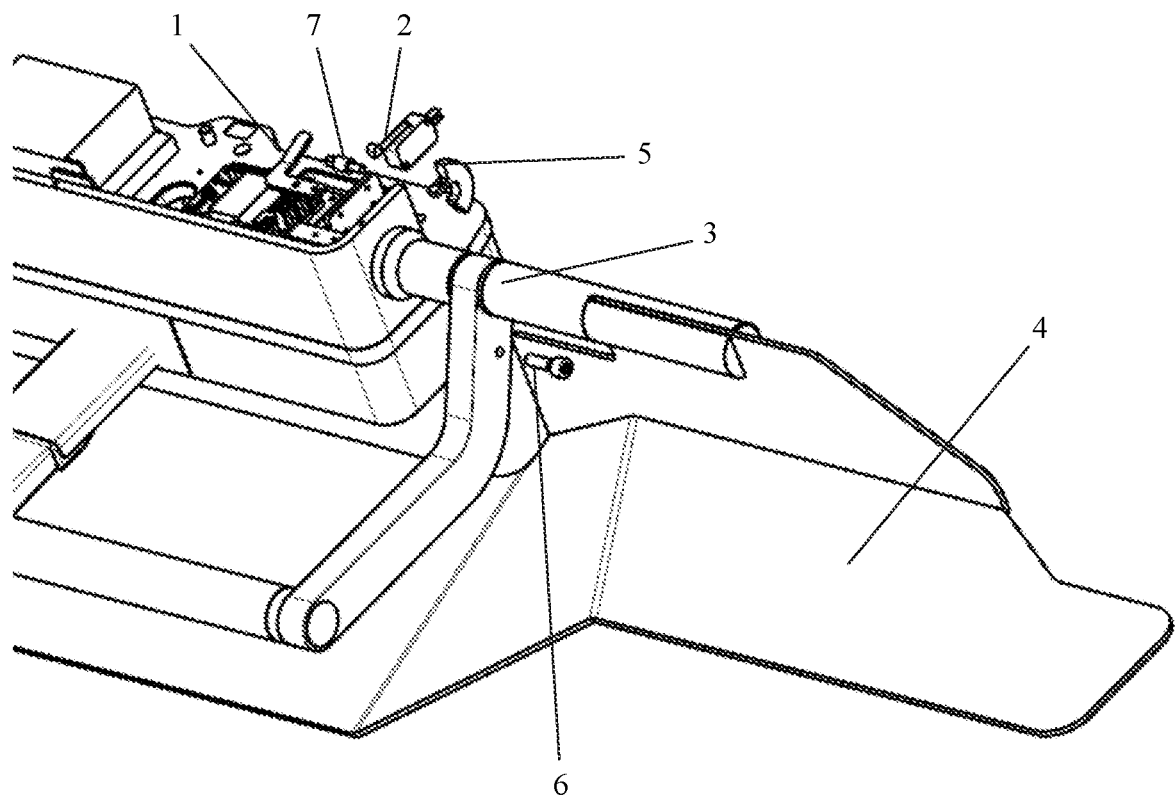
FIG. 2 is a partial schematic exploded view of a vertical protective device for a medical display hanger according to an embodiment of the present invention.
Figure 3:
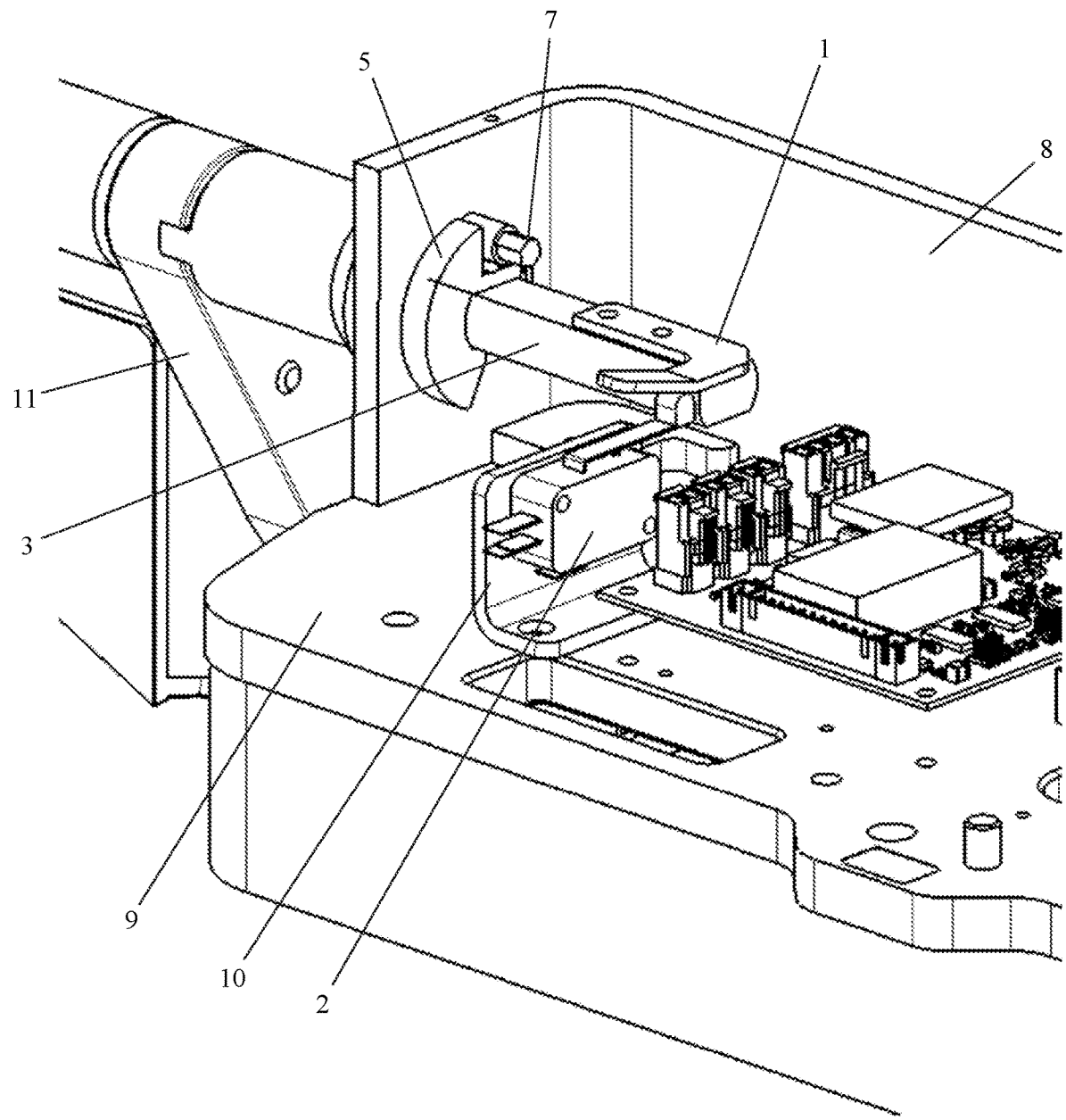
FIG. 3 is a partial schematic perspective view of a vertical protective device for a medical display hanger according to an embodiment of the present invention.

FIG. 1 is a schematic installation diagram of a vertical protective device for a medical display hanger according to an embodiment of the present invention. FIG. 2 is a partial schematic exploded view of a vertical protective device for a medical display hanger according to an embodiment of the present invention. FIG. 3 is a partial schematic perspective view of a vertical protective device for a medical display hanger according to an embodiment of the present invention. It should be noted that, in order to show the details more clearly, viewing directions of FIGS. 2 and 3 are different, FIG. 2 is viewed from a front right direction of the vertical protective device, and FIG. 3 is viewed from a rear left direction of the vertical protective device.

As shown in FIGS. 1-3, according to an embodiment of the present invention, a vertical protective device 20 for a medical display hanger includes a contact piece 1, a microswitch 2, a rotating shaft 3, and a vertical protective plate 4.

The contact piece 1 is connected (e.g., threadedly connected) to one end of the rotating shaft 3, the vertical protective plate 4 is connected (e.g., threadedly connected) to the other end of the rotating shaft 3, and the microswitch 2 is arranged on (e.g., fastened via a screw to) a microswitch support 10.

When a collision of the vertical protective plate 4 happens, the rotating shaft 3 drives the contact piece 1 to rotate, and the contact piece 1 triggers the microswitch 2, so as to control the medical display hanger 30 to stop moving or immediately rise.

According to the above technical solution, the vertical protective device for a medical display hanger of the present invention can achieve the following beneficial technical effect: when an accidental collision of the medical display hanger happens in a substantially vertical direction, the medical display hanger can effectively come to an emergency stop or avoid.

Specifically, the present invention adopts a vertical protective device for a medical display hanger, when an accidental collision of the medical display hanger happens in a substantially vertical direction, the vertical protective plate rotates upwardly, such that the rotating shaft drives the contact piece to rotate, the contact piece triggers the microswitch, and the microswitch sends a signal to a controller (that is, the vertical protective device for the medical display hanger further includes a controller that communicates with the microswitch), so as to control the medical display hanger to stop the descending movement or immediately rise, that is, the instant stop or avoidance of the medical display hanger can be realized.

Preferably, as shown in FIG. 1, the vertical protective device 20 for the medical display hanger is installed at the bottom of the medical display hanger 30.

Preferably, when the medical display hanger 30 is lowered and causes the collision of the vertical protective plate 4, the medical display hanger 30 is controlled to stop moving.

According to the above technical solution, the vertical protective device for a medical display hanger of the present invention can achieve the following beneficial technical effect: when an accidental collision of the medical display hanger happens in a substantially vertical direction, the medical display hanger can effectively emergency stop.

Preferably, when an operating table rises (the medical display hanger 30 is stationary) and causes the collision of the vertical protective plate 4, the medical display hanger 30 is controlled to rise immediately.

According to the above technical solution, the vertical protective device for a medical display hanger of the present invention can achieve the following beneficial technical effect: when an accidental collision of the medical display hanger happens in a substantially vertical direction, the medical display hanger can effectively avoid.

That is to say, when the medical display hanger 30 is lowered and causes the collision of the vertical protective plate 4, the medical display hanger 30 is controlled to stop the descending movement, and if the medical staff continue to press a down button, the descending movement of the medical display hanger 30 will not take effect, and the down button will return to a normal state after the collision is released. When the operating table rises and causes the collision of the vertical protective plate 4, the medical display hanger 30 is controlled to rise immediately, and the rising speed of the medical display hanger should be greater than the rising speed of the operating table to avoid the accidental collision until the collision is released.

Preferably, as shown in FIGS. 2 and 3, the vertical protective device for the medical display hanger further includes a rotating shaft support 8, and the rotating shaft 3 is provided with one end passing through the rotating shaft support 8.

According to the above technical solution, the vertical protective device for a medical display hanger of the present invention can achieve the following beneficial technical effect: the rotation of the rotating shaft can be made stable, so that the medical display hanger can more effectively come to an emergency stop or avoid.

Preferably, as shown in FIGS. 2 and 3, the vertical protective device for the medical display hanger further includes an internal limiting post 7 and a limiting block 5, the internal limiting post 7 is arranged on (e.g., threadedly connected to) an inside face of the rotating shaft support 8, and the limiting block 5 is arranged on (e.g., threadedly connected to) the rotating shaft 3 and opposite the internal limiting post 7.

When no collision of the vertical protective plate 4 happens, the limiting block 5 abuts against the internal limiting post 7 due to the gravity of the vertical protective plate 4.

According to the above technical solution, the vertical protective device for a medical display hanger of the present invention can achieve the following beneficial technical effect: when no collision of the vertical protective plate happens, the vertical protective plate can be kept in a substantially horizontal state.

Preferably, as shown in FIGS. 2 and 3, the limiting block 5 is a specially-shaped limiting block.

According to the above technical solution, the vertical protective device for a medical display hanger of the present invention can achieve the following beneficial technical effect: when no collision of the vertical protective plate happens, the abutment of the limiting block against the internal limiting post can be made more robust, so that the vertical protective plate can be better kept in a substantially horizontal state.

Preferably, as shown in FIGS. 2 and 3, the vertical protective device for the medical display hanger further includes a handle support 11 and an external limiting post 6, the handle support 11 is connected (e.g., threadedly connected) to the rotating shaft support 8, and the external limiting post 6 is arranged on (e.g., threadedly connected to) the handle support 11.

When the collision of the vertical protective plate 4 happens and the vertical protective plate rotates upwardly to a maximum upward rotation angle, the vertical protective plate 4 interferes with the external limiting post 6 to realize limiting.

According to the above technical solution, the vertical protective device for a medical display hanger of the present invention can achieve the following beneficial technical effect: the upward rotation angle of the vertical protective plate can be restricted within a certain range, so that the microswitch can be effectively triggered, and the microswitch can also be prevented from being damaged due to excessive contact.

Preferably, the maximum upward rotation angle of the vertical protective plate 4 is 2-5 degrees.

According to the above technical solution, the vertical protective device for a medical display hanger of the present invention can achieve the following beneficial technical effect: by setting an appropriate maximum upward rotation angle of the vertical protective plate, the microswitch can be effectively triggered, and the microswitch can also be prevented from being damaged due to excessive contact.

Preferably, the maximum upward rotation angle of the vertical protective plate 4 is 3.5 degrees.

According to the above technical solution, the vertical protective device for a medical display hanger of the present invention can achieve the following beneficial technical effect: by setting an optimal maximum upward rotation angle of the vertical protective plate, the microswitch can be effectively triggered, and the microswitch can also be prevented from being damaged due to excessive contact.

Preferably, as shown in FIGS. 2 and 3, the vertical protective device for the medical display hanger further includes a bottom plate 9, the bottom plate 9 is connected (e.g., threadedly connected) to the rotating shaft support 8, and the microswitch support 10 is arranged on (e.g., fastened via a screw to) the bottom plate 9.

According to the above technical solution, the vertical protective device for a medical display hanger of the present invention can achieve the following beneficial technical effect: the microswitch can be installed in a rational position, so that the microswitch can be effectively triggered.

Preferably, when the operating table rises and causes the collision of the vertical protective plate 4, the medical display hanger 30 is controlled to rise immediately at a rising speed of 25-30 mm/s.

According to the above technical solution, the vertical protective device for a medical display hanger of the present invention can achieve the following beneficial technical effect: when an accidental collision of the medical display hanger happens in a substantially vertical direction, the medical display hanger can more effectively avoid.

More preferably, when the operating table rises and causes the collision of the vertical protective plate 4, the medical display hanger 30 is controlled to rise immediately at a rising speed of 28 mm/s.

Of course, the rising speed of 25-30 mm/s of the medical display hanger is only a preferred speed range adopted by the vertical protective device for the medical display hanger of the present application, those skilled in the art can understand on the basis of the disclosure of the present application that other suitable rising speeds of the medical display hanger may also be used, as long as the rising speed of the medical display hanger is greater than the rising speed of the operating table to avoid the accidental collision, without departing from the scope of protection of the claims of the present application.

The specific implementations of the present invention are described above. However, it would be understood by those skilled in the art that the above specific implementations do not constitute the limitations on the present invention, and those skilled in the art may make various modifications on the basis of the above disclosure without departing from the scope of the present invention.

The invention claimed is:

1. A vertical protective device for a medical display hanger, wherein the vertical protective device for the medical display hanger comprises a contact piece, a microswitch, a rotating shaft and a vertical protective plate, wherein the contact piece is connected to one end of the rotating shaft, the vertical protective plate is connected to the other end of the rotating shaft, and the microswitch is arranged on a microswitch support; and when a collision of the vertical protective plate happens, the rotating shaft drives the contact piece to rotate, and the contact piece triggers the microswitch, so as to control the medical display hanger to stop moving or immediately rise;

wherein the vertical protective device for the medical display hanger further comprises a rotating shaft support, and the rotating shaft is provided with one end passing through the rotating shaft support;

wherein the vertical protective device for the medical display hanger further comprises an internal limiting post and a limiting block, the internal limiting post is arranged on an inside face of the rotating shaft support, and the limiting block is arranged on the rotating shaft and opposite the internal limiting post; and when no collision of the vertical protective plate happens, the limiting block abuts against the internal limiting post due to the gravity of the vertical protective plate.

2. The vertical protective device for a medical display hanger of claim 1, wherein when the medical display hanger is lowered and causes the collision of the vertical protective plate, the medical display hanger is controlled to stop moving.

3. The vertical protective device for a medical display hanger of claim 1, wherein when an operating table rises and causes the collision of the vertical protective plate, the medical display hanger is controlled to rise immediately.

4. The vertical protective device for a medical display hanger of claim 1, wherein the vertical protective device for the medical display hanger further comprises a handle support and an external limiting post, the handle support is connected to the rotating shaft support, and the external limiting post is arranged on the handle support; and when the collision of the vertical protective plate happens and the vertical protective plate rotates upwardly to a maximum upward rotation angle, the vertical protective plate interferes with the external limiting post to realize limiting.

5. The vertical protective device for a medical display hanger of claim 4, wherein the maximum upward rotation angle of the vertical protective plate is 2-5 degrees.

6. The vertical protective device for a medical display hanger of claim 5, wherein the maximum upward rotation angle of the vertical protective plate is 3.5 degrees.

7. The vertical protective device for a medical display hanger of claim 1, wherein the vertical protective device for the medical display hanger further comprises a bottom plate, the bottom plate is connected to the rotating shaft support, and the microswitch support is arranged on the bottom plate.

8. The vertical protective device for a medical display hanger of claim 3, wherein when the operating table rises and causes the collision of the vertical protective plate, the medical display hanger is controlled to rise immediately at a rising speed of 25-30 mm/s.

* * * * *